(12) United States Patent
Kitamoto et al.

(10) Patent No.: US 11,246,488 B2
(45) Date of Patent: Feb. 15, 2022

(54) MEDICAL IMAGING DEVICE

(71) Applicant: Shimadzu Corporation, Kyoto (JP)

(72) Inventors: Hiroyuki Kitamoto, Kyoto (JP);
Kazushige Tachibana, Kyoto (JP);
Akihiro Ishikawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 259 days.

(21) Appl. No.: 16/200,947

(22) Filed: Nov. 27, 2018

(65) Prior Publication Data
US 2020/0163552 A1 May 28, 2020

(51) Int. Cl.
*A61B 5/00* (2006.01)

(52) U.S. Cl.
CPC .......... *A61B 5/0071* (2013.01); *A61B 5/7475* (2013.01); *A61B 2560/045* (2013.01); *A61B 2560/0437* (2013.01); *A61B 2562/0233* (2013.01)

(58) Field of Classification Search
CPC ... A61B 5/0071; A61B 5/7475; A61B 5/0033; A61B 2560/045; A61B 2560/0437; A61B 2560/0233
See application file for complete search history.

(56) References Cited

U.S. PATENT DOCUMENTS

| | | | |
|---|---|---|---|
| 8,681,116 B2 * | 3/2014 | Merritt | A61B 5/7435 345/173 |
| 2009/0062662 A1 * | 3/2009 | Zuluaga | A61B 1/00048 600/478 |
| 2009/0261992 A1 | 10/2009 | Song | |
| 2010/0056913 A1 * | 3/2010 | Hirakui | A61B 8/4405 600/437 |
| 2011/0256024 A1 * | 10/2011 | Cole | G01N 33/48792 422/68.1 |
| 2017/0027541 A1 * | 2/2017 | Henderson | A61B 8/4427 |

FOREIGN PATENT DOCUMENTS

| | | |
|---|---|---|
| JP | 2009-259243 A | 11/2009 |
| JP | 2015-188559 A | 11/2015 |
| JP | 2017124035 A * | 7/2017 |

OTHER PUBLICATIONS

Office Action dated Jul. 2, 2019, in corresponding Japanese Application No. 2016-105732; 12 pages.

* cited by examiner

*Primary Examiner* — Sean D Mattson
(74) *Attorney, Agent, or Firm* — Maier & Maier, PLLC (57) ABSTRACT

A medical imaging device. The medical imaging device includes a device body and an operation unit. The device body has a first mating portion on its upper surface, and the operation unit has a second mating portion configured to movably mate with the first mating portion. The operation unit is provided separately from the device body, and the operation unit is configured to operate the device.

10 Claims, 4 Drawing Sheets

MEDICAL IMAGING DEVICE

BACKGROUND

The present disclosure relates to a medical imaging device, and specifically relates to a medical imaging device having a detector detecting light from the inside of a subject body.

Medical imaging devices with a detector for detecting light from the inside of a subject body are widely known including, for example, the device described in Japanese Unexamined Patent Publication No. 2015-188559.

The medical imaging device described in Japanese Unexamined Patent Publication No. 2015-188559 irradiates a subject with infrared from an infrared source to excite fluorochrome injected into the subject body. Light (infrared beams) generated from the fluorochrome by infrared radiation is imaged by a camera, and the image taken by the camera is displayed on a display. The medical imaging device further includes an input unit (operation unit) and is operated using the input unit.

Some conventional medical imaging devices, such as the device described in Japanese Unexamined Patent Publication No. 2015-188559, have an input unit provided separately from the device body. During use of such a medical imaging device, the input unit separately provided from the device body is sometimes put on a flat upper surface of the device body. The input unit may also be put on the flat upper surface of the device body with the intention of storing the input unit or of keeping the input unit during move of the device to another room.

In such a medical imaging device as described in Japanese Unexamined Patent Publication No. 2015-188559, the flat upper surface of the device body is sometimes used as a place to deposit a monitor, documents (such as charts), and other accessories. When those things accidentally contact the input unit placed on the upper surface of the device body, the input unit may slip off the upper surface. In other words, the input unit (operation unit) is less likely to be rested in a stable condition.

SUMMARY

In view of the foregoing background, it is an object of the present disclosure to provide a medical imaging device that allows an operation unit to be rested in a stable condition.

To overcome the above problems, a medical imaging device of a first aspect of the present disclosure includes: a light source unit configured to irradiate a contrast agent inside a subject body with light, a detection unit configured to detect light generated by radiation of light from the light source unit and emitted from the inside of the subject body, a device body provided with the light source unit and the detection unit, and an operation unit configured to be movable and provided separately from the device body to operate the device. The device body has a first mating portion on its upper surface, and the operation unit has a second mating portion configured to movably mate with the first mating portion.

In the medical imaging device of the first aspect of the present disclosure, as described above, the device body has the first mating portion on its upper surface, and the operation unit has the second mating portion configured to movably mate with the first mating portion. This configuration allows the operation unit to be engaged with the upper surface of the device body, and therefore can avoid the operation unit from slipping off the upper surface when something, such as an accessory, on the upper surface of the device body accidentally contacts the operation unit. The operation unit thus can be rested on the medical imaging device in a stable condition.

In the medical imaging device of the first aspect, preferably, the device body has the first mating portion on its upper surface, and the operation unit has the second mating portion configured to movably mate with the recessed first mating portion. The first mating portion is recessed and the second mating portion protrudes. This configuration can flatten the upper surface of the device body, unlike a configuration in which the protruding first mating portion is formed on an upper surface of a device body. The flat upper surface allows things, such as accessories, other than the operation unit to be easily placed on the upper surface of the device body.

Preferably, the recessed first mating portion is slot-shaped and substantially linearly extended along a predetermined direction, and the protruding second mating portion is substantially linearly extended along the predetermined direction and is configured to be slidably movable along the slot-shaped first mating portion while mated with the slot-shaped first mating portion. This configuration can increase an empty region (region for placing accessories and others) on the upper surface of the device body by sliding the operation unit from the center portion, or nearby area, to an end portion of the upper surface of the device body. A user can move the operation unit to a location convenient for operation.

In the medical imaging device having the slot-shaped first mating portion, preferably, the device body is configured to be movable, and the slot-shaped first mating portion is substantially linearly extended along a direction perpendicular to the direction of move of the device body. The slot-shaped first mating portion can stop the operation unit from shifting (moving) in the direction of move of the device body, with move of the device body.

In the medical imaging device having the slot-shaped first mating portion, preferably, the operation unit is connected with the device body using a cable, and the slot-shaped first mating portion is substantially linearly extended along a direction perpendicular to a direction in which the operation unit is pulled by the weight of the cable. The slot-shaped first mating portion arranged as above can stop the operation unit from being pulled and moved by the weight of the cable.

In the medical imaging device having the slot-shaped first mating portion, preferably, the length of the slot-shaped first mating portion in a direction along the predetermined direction is larger than the length of the protruding second mating portion in a direction along the predetermined direction. This configuration allows the operation unit to move a comparatively large distance along the predetermined direction.

In the medical imaging device having the slot-shaped first mating portion, preferably, the device body includes side surfaces perpendicular to the upper surface, and the slot-shaped first mating portion has wall portions at an end and the other end in a direction along the predetermined direction, for avoiding the respective ends of the slot-shaped first mating portion from reaching the side surfaces. This configuration can stop the operation unit from sliding and slipping off the device body, unlike a configuration in which the slot-shaped first mating portion is continuous with the side surface.

In the medical imaging device having the slot-shaped first mating portion, preferably, the slot-shaped first mating portion has corners formed near an opening end surface of the first mating portion and aligned in a direction perpendicular to the predetermined direction. The corner is chamfered to be round. The chamfered rounded corners formed as above allow the protruding second mating portion to easily mate with the slot-shaped first mating portion by guiding the protruding second mating portion in the process of mating with the slot-shaped first mating portion.

In the medical imaging device of the first aspect, preferably, the device body has the first mating portion including a plurality of first mating portions on its upper surface. This configuration allows the operation unit to be rested in a stable condition at a plurality of locations on the upper surface of the device body.

In the medical imaging device of the first aspect, preferably, a contrast agent inside a subject body contains a fluorescent agent, and a light source unit is configured to irradiate the fluorescent agent inside the subject body with near-infrared excitation light, and a detection unit is configured to detect near-infrared fluorescence generated by radiation of the near-infrared excitation light from the light source unit and emitted from the inside of the subject body. For a medical imaging device detecting near-infrared fluorescence from the inside of a subject body, the above configuration allows the operation unit to be rested in a stable condition.

DETAILED DESCRIPTION

Embodiments of the present disclosure will now be described with reference to the drawings.

Embodiment

A near-infrared fluorescent imaging device 100 of an embodiment of the present disclosure will now be described with reference to FIG. 1 to FIG. 6. The near-infrared fluorescent imaging device 100 is used in, for example, angiography for surgery. The near-infrared fluorescent imaging device 100 is an example of a "medical imaging device" in the appended claims.

Figure 1:
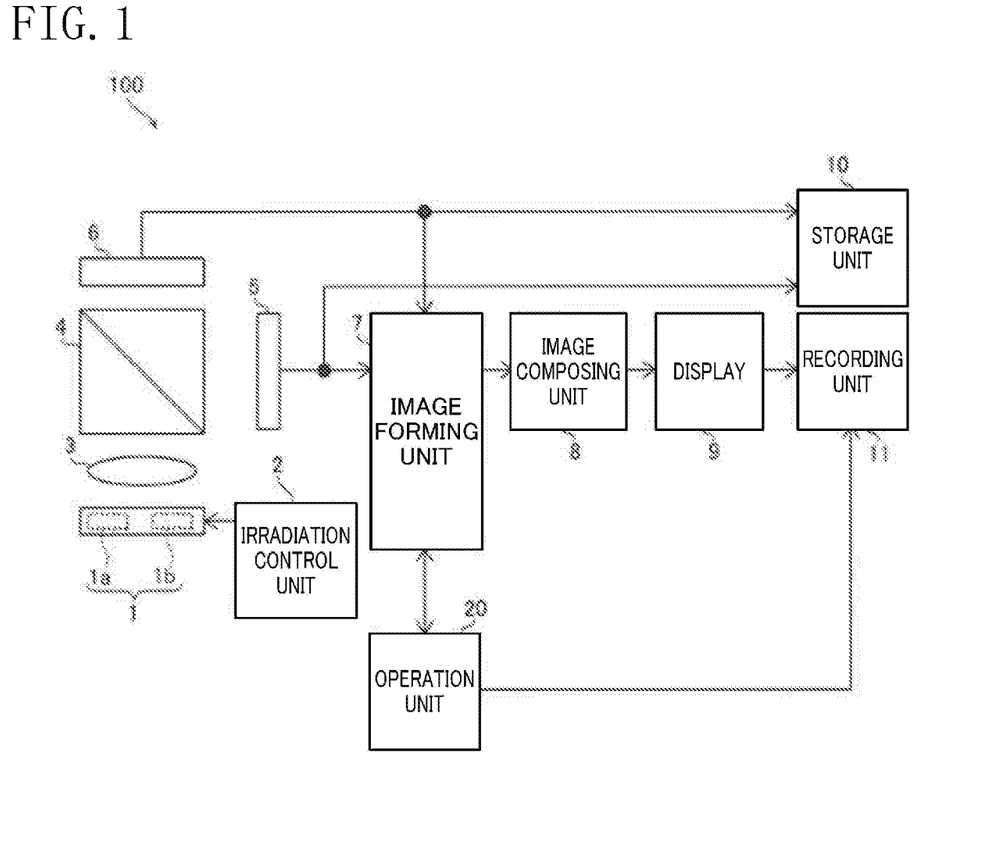
FIG. 1 is a block diagram of a near-infrared fluorescent imaging device according to an embodiment of the present disclosure.

As illustrated in FIG. 1, the near-infrared fluorescent imaging device 100 includes a light source 1. The light source 1 includes a first light source 1a irradiating a subject (not illustrated) with white light and a second light source 1b irradiating a fluorescent agent inside the subject body with near-infrared excitation light. The fluorescent agent is indocyanine green (ICG) as a fluorescent dye. The near-infrared excitation light is near-infrared having a wavelength of about 810 nm. With indocyanine green irradiated with the near-infrared having a wavelength of about 810 nm, near-infrared fluorescence having a wavelength of about 845 nm is generated from the indocyanine green. The white light emitted from the first light source 1a is reflected on the subject as reflection light. The fluorescent agent is an example of a "contrast agent" in the appended claims. The second light source 1b is an example of a "light source unit" in the appended claims.

The near-infrared fluorescent imaging device 100 includes an irradiation control unit 2. The irradiation control unit 2 controls, for example, emission and stop of emission of light (white light and near-infrared excitation light) from the light source 1.

A zoom lens 3 is provided near the light source 1. The zoom lens 3 receives reflection light (visible light) from the subject and near-infrared fluorescence generated from indocyanine green inside the subject body.

A prism 4 is provided near the zoom lens 3. The prism 4 receives light (white light and near-infrared excitation light) from the zoom lens 3. The prism 4 has a function of separating the light from the zoom lens 3 between the reflection light (visible light) from the subject and near-infrared fluorescence generated from indocyanine green in the subject body.

The near-infrared fluorescent imaging device 100 includes a visible light sensor 5 detecting visible light separated by the prism 4. The near-infrared fluorescent imaging device 100 further includes a near-infrared fluorescent sensor 6 detecting near-infrared fluorescence, generated by radiation of the near-infrared excitation light from the second light source 1b and emitted from the inside of a subject body. The near-infrared fluorescent sensor 6 is an example of a "detection unit" in the appended claims.

The near-infrared fluorescent imaging device 100 includes an image forming unit 7. The image forming unit 7 receives inputs of visible light detected by the visible light sensor 5 and near-infrared fluorescence detected by the near-infrared fluorescent sensor 6. The image forming unit 7 forms an image of 24 bits (=3×8) composed of three colors of RGB (red, green, blue), based on the visible light detected by the visible light sensor 5. The image forming unit 7 forms an image of eight bits based on the near-infrared fluorescence detected by the near-infrared fluorescent sensor 6.

The near-infrared fluorescent imaging device 100 includes an image composing unit 8. The image composing unit 8 creates a composite image 203 by composing an image (visible image) 201 (see FIG. 2) based on visible light and an image (near-infrared fluorescence image) 202 based on near-infrared fluorescence, which are formed by the image forming unit 7.

Figure 2:
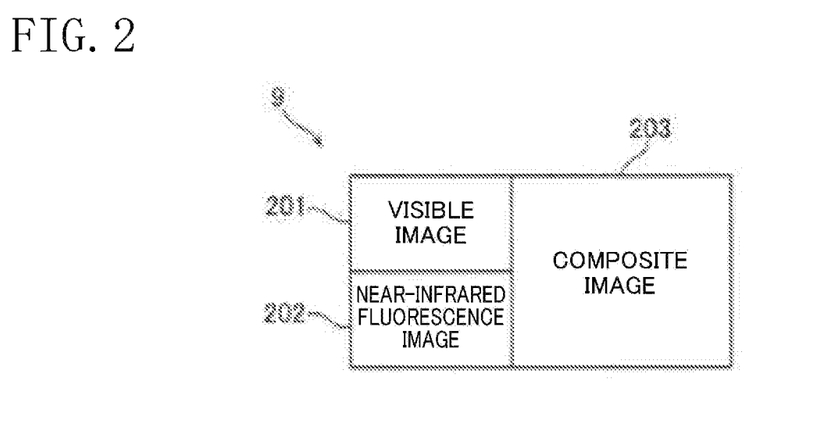
FIG. 2 is a drawing illustrating an image displayed on a display of the near-infrared fluorescent imaging device according to the embodiment of the present disclosure.

The near-infrared fluorescent imaging device 100 includes a display 9. As illustrated in FIG. 2, the display 9 displays the image 201 based on visible light and the image 202 based on near-infrared fluorescence, which are formed by the image forming unit 7, and the composite image 203.

As illustrated in FIG. 1, the near-infrared fluorescent imaging device 100 includes a storage unit 10. The storage unit 10 stores visible light (signal) detected by the visible light sensor 5 and near-infrared fluorescence (signal) detected by the near-infrared fluorescent sensor 6.

The near-infrared fluorescent imaging device 100 has a recording unit 11. The recording unit 11 records images displayed on the display 9.

The near-infrared fluorescent imaging device 100 includes an operation unit 20. The operation unit 20 is used for operation of the near-infrared fluorescent imaging device 100. The operation unit 20 is used for operation of, for example, emission and stop of emission of light from the light source 1, control of brightness and sensitivity, and adjustment of a display format of an image displayed on the display 9.

Figure 3:
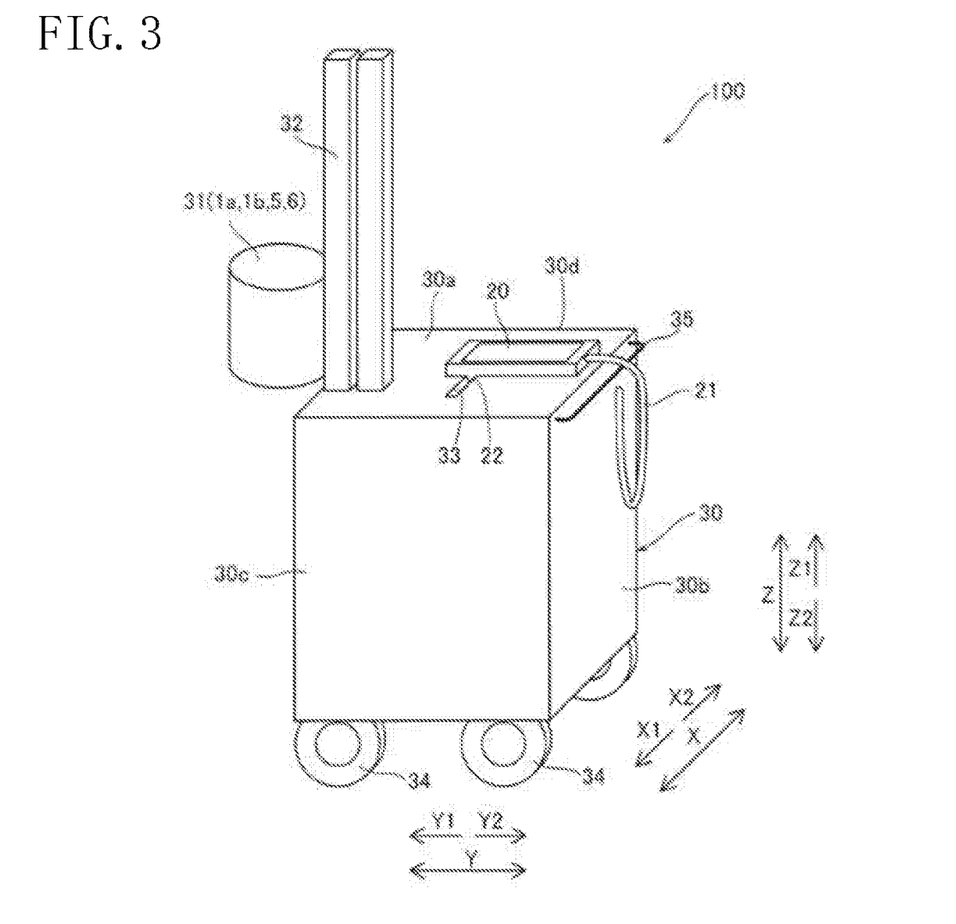
FIG. 3 is a perspective view of the near-infrared fluorescent imaging device according to the embodiment of the present disclosure.

As illustrated in FIG. 3, the near-infrared fluorescent imaging device 100 includes a device body 30 having the first light source 1a, the second light source 1b, the visible light sensor 5, the near-infrared fluorescent sensor 6, and others. More specifically, the first light source 1a, the second light source 1b, the visible light sensor 5, the near-infrared fluorescent sensor 6, and other units are disposed in an lighting and imaging unit 31. The device body 30 further has an arm unit 32. The lighting and imaging unit 31 is vertically movably attached to the arm unit 32.

The operation unit 20 is movable and provided separately from the device body 30. The operation unit 20 is connected with the device body 30 through a cable 21. The operation unit 20 has a substantially flat upper surface (a surface in the Z1 direction), and operation buttons (not illustrated) are formed on the substantially flat upper surface of the operation unit 20.

In this embodiment, as illustrated in FIG. 3 to FIG. 6, the device body 30 has a recess 33 on an upper surface 30a thereof. The operation unit 20 has a protrusion 22 configured to movably mate with the recess 33. More specifically, the upper surface 30a of the device body 30 is flat, and the recess 33 is formed on the flat upper surface 30a. The protrusion 22 is formed on a lower surface 20a of the operation unit 20. The recess 33 is an example of a "first mating portion" in the appended claims. The protrusion 22 is an example of a "second mating portion" in the appended claims.

Figure 5:
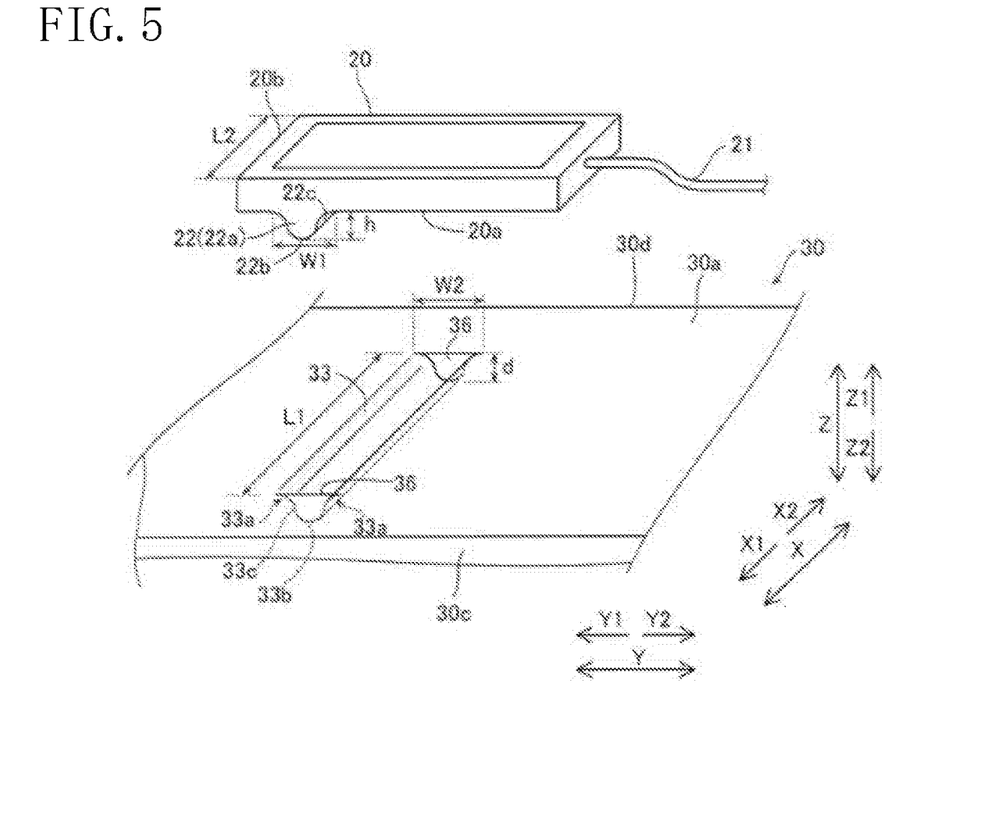
FIG. 5 is a drawing of an operation unit, of the near-infrared fluorescent imaging device according to the embodiment of the present disclosure, before mating with (fitting in) a recess.
Figure 6:
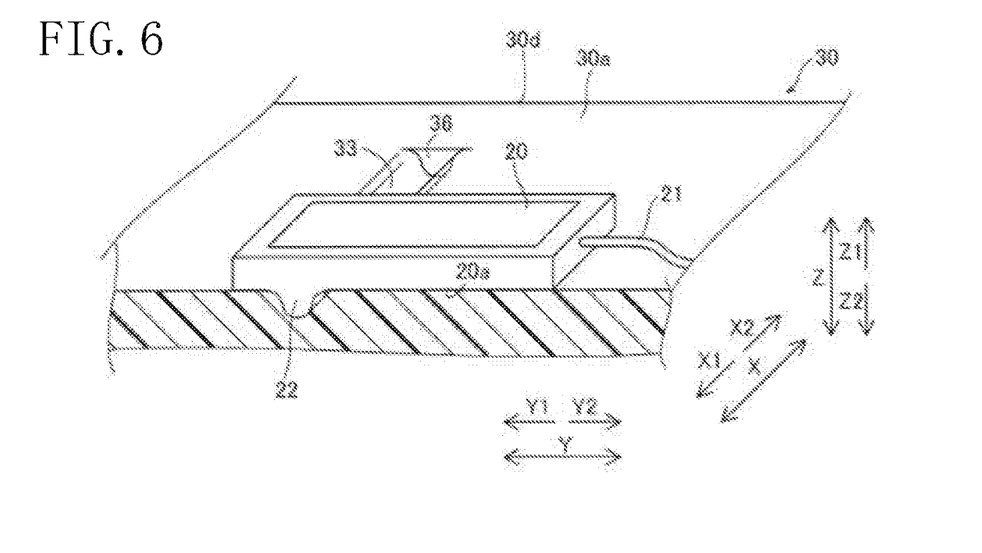
FIG. 6 is a drawing (a sectional view) of the operation unit, of the near-infrared fluorescent imaging device according to the embodiment of the present disclosure, after mating with (fitting in) the recess.

In this embodiment, as illustrated in FIG. 5, the recess 33 is slot-shaped and is substantially linearly extended along a predetermined direction (the X direction). The protrusion 22 is substantially linearly extended along the predetermined direction (the X direction) and is slidably movable along the recess 33 while mated with the slot-shaped recess 33. More specifically, the protrusion 22 has a width W1 in the X direction that is substantially equal to a width W2 of the recess 33 in the X direction or is slightly smaller than the same, which allows the protrusion 22 to fit in the recess 33. The protrusion 22 has a height h of protrusion in the Z direction that is substantially equal to a depth d of the recess 33 in the Z direction or is slightly smaller than the same. With this configuration, as illustrated in FIG. 6, the lower surface 20a of the operation unit 20 contacts the flat upper surface 30a with the protrusion 22 mating with the recess 33.

In this embodiment, as illustrated in FIG. 5, the recess 33 has a length L1 along the predetermined direction (the X direction) that is larger than a length L2 of the protrusion 22 in the predetermined direction (the X direction). The operation unit 20 is substantially rectangular, and the protrusion 22 is arranged along a short side 20b of the substantially rectangular operation unit 20. The protrusion 22 is arranged from an end to the other end of the operation unit 20 in the X direction. The length L2 of the protrusion 22 along the predetermined direction is substantially equal to the length of the short side 20b of the operation unit 20. The length L1 of the recess 33 in the predetermined direction is, for example, at least twice as large as the length L2 of the protrusion 22 along the predetermined direction. This configuration allows the operation unit 20 to slide a distance larger than the length of the short side 20b of the operation unit 20, along the recess 33. In the case with a plurality of operation units 20, one recess 33 can receive two operation units 20.

As illustrated in FIG. 3, the device body 30 is movable. More specifically, the device body 30 is provided with casters 34 on its lower surface. The device body 30 further has a handle 35 on the surface in the Y2 direction. A user holds the handle 35 and pushes the device body 30 to move the device body 30 in the Y1 direction. In this embodiment, the slot-shaped recess 33 is substantially linearly extended along a direction perpendicular to a direction (Y1 direction) of move of the device body 30. In other words, the slot-shaped recess 33 is extended along the X direction perpendicular to the direction (the Y1 direction) of move of the device body 30.

In this embodiment, the slot-shaped recess 33 is substantially linearly extended along a direction perpendicular to a direction in which the operation unit 20 is pulled by the weight of the cable 21 connecting between the operation unit 20 and the device body 30. Specifically, the cable 21 connects an end of the operation unit 20 in the Y2 direction and a side surface 30b of the device body 30 in the Y2 direction. The cable 21 hangs from the upper surface 30a of the device body 30 with the protrusion 22 of the operation unit 20 mating with the recess 33 of the device body 30. The operation unit 20 is therefore pulled in the Y2 direction by the weight of the cable 21. The slot-shaped recess 33 is substantially linearly extended along the X direction perpendicular to the Y2 direction in which the operation unit 20 is pulled.

Figure 4:
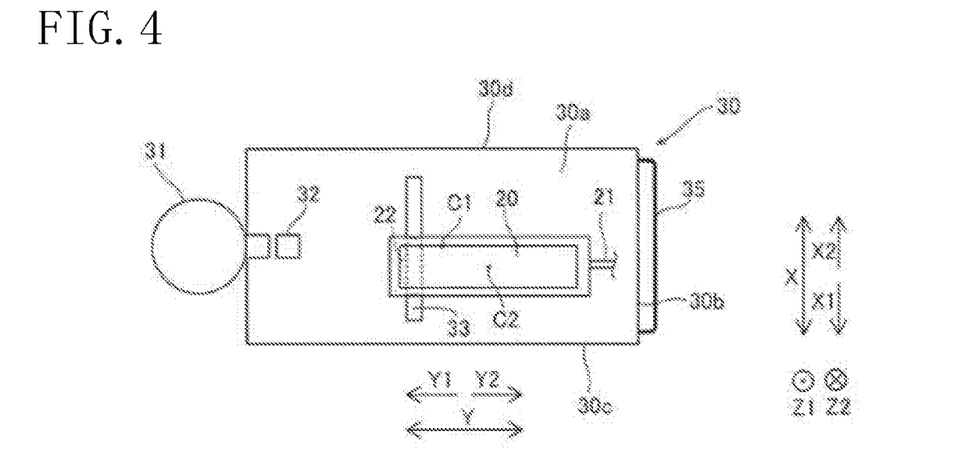
FIG. 4 is a top view of the near-infrared fluorescent imaging device according to the embodiment of the present disclosure.

As illustrated in FIG. 4, in plan view, the slot-shaped recess 33 is formed remote (or nearby a center C1), toward the Y1 direction, from the center C1 of the upper surface 30a of the device body 30 in the Y direction. In plan view, the protrusion 22 of the operation unit 20 is formed closer to an end (in the Y1 direction) opposite to the other end (in the Y2 direction), having the cable 21 connected, of the operation unit 20 with respect to a center C2 of the operation unit 20 in the Y direction.

As illustrated in FIG. 5, the device body 30 includes side surfaces 30c and 30d each arranged perpendicular to the upper surface 30a. The side surfaces 30c and 30d are surfaces in the X1 direction and in the X2 direction of the device body 30, respectively. In this embodiment, the slot-shaped recess 33 has wall portions 36 at an end and the other end along the predetermined direction (the X direction) of the recess 33, for avoiding the respective ends of the recess 33 from reaching the side surfaces 30c and 30d. The wall portion 36 is a flat surface along the Y-Z plane. Similarly, the protrusion 22 of the operation unit 20 has flat end surfaces 22a in the Y1 direction and in the Y2 direction along the Y-Z plane. The end surface 22a of the protrusion 22 and the wall portion 36 of the recess 33 are configured to contact each other surface-to-surface.

In this embodiment, the slot-shaped recess 33 have chamfered rounded corners 33a, which are formed near the opening end surface (the Z1 direction) and aligned in a direction (the Y direction) perpendicular to the predetermined direction. More specifically, the slot-shaped recess 33 includes a bottom 33b and inner side surfaces 33c continuously extended from respective ends of the bottom 33b in the Y1 direction and the Y2 direction, toward the Z1 direction. The inner side surface 33c of the recess 33 and the upper surface 30a of the device body 30 are connected with each other with a round (radius) edge formed therebetween. Likewise, the bottom 33b and the inner side surface 33c are connected with each other with a round (radius) edge formed therebetween.

The protrusion 22 is shaped to substantially conform (correspond) to the shapes of the bottom 33b and the inner side surfaces 33c of the recess 33. The protrusion 22 has front end 22b and outer side surfaces 22c connected with each other through round (radius) edges formed therebetween. In other words, the protrusion 22 is chamfered to correspond to the shape of the recess 33. This configuration allows the protrusion 22 to mate with the recess 33 with a minimum gap therebetween.

Effects of this Embodiment

This embodiment can exert the following advantageous effects.

In this embodiment, as described above, the device body 30 has the recess 33 on the upper surface 30a, and the operation unit 20 has the protrusion 22 configured to movably mate with the recess 33. This configuration allows the operation unit 20 to be engaged with the upper surface 30a of the device body 30 and keeps the operation unit 20 from slipping off the upper surface 30a when things such as accessories placed on the upper surface 30a of the device body 30 accidentally contact the operation unit 20. The operation unit 20 therefore can be rested in a stable condition on the near-infrared fluorescent imaging device 100.

This configuration allows the upper surface 30a of the device body 30 to be flattened, unlike a configuration in which a protruding engagement unit is formed on the upper surface 30a of the device body 30. This configuration therefore allows things, such as accessories, other than the operation unit 20 to be easily placed on the upper surface 30a of the device body 30.

In this embodiment, as described above, the recess 33 is slot-shaped and is substantially linearly extended along the predetermined direction. The protrusion 22 is substantially linearly extended along the predetermined direction and is slidably movable along the slot-shaped recess 33 while mated with the slot-shaped recess 33. Sliding the operation unit 20 from the center portion, or nearby area, to an end portion of the upper surface 30a of the device body 30 can increase an empty region (region for placing accessories and others) on the upper surface 30a of the device body 30. Furthermore, a user can move the operation unit 20 to a position convenient for operation.

In this embodiment, as described above, the slot-shaped recess 33 is substantially linearly extended along a direction perpendicular to the direction of move of the device body 30. The slot-shaped recess 33 therefore can stop the operation unit 20 from shifting (moving) in the direction of move of the device body 30, with move of the device body 30.

In this embodiment, as described above, the slot-shaped recess 33 is substantially linearly extended along a direction perpendicular to a direction in which the operation unit 20 is pulled by the weight of the cable 21. The slot-shaped recess 33 therefore can stop the operation unit 20 from being pulled and moved by the weight of the cable 21.

In this embodiment, as described above, the length L1 of the recess 33 along the predetermined direction is larger than the length L2 of the protrusion 22 along the predetermined direction. This configuration allows the operation unit 20 to move a comparatively large distance along the predetermined direction.

In this embodiment, as described above, the slot-shaped recess 33 has wall portions 36 at an end and the other end along the predetermined direction of the recess 33, for avoiding the respective ends of the recess 33 from reaching the side surfaces 30c and 30d. This configuration can avoid the operation unit 20 from sliding and slipping off the device body 30, unlike a configuration in which the slot-shaped recess 33 is continuous with the side surfaces 30c and 30d.

In this embodiment, as described above, the slot-shaped recess 33 has corners 33a, formed near the opening end surface of the recess 33 and aligned in a direction perpendicular to the predetermined direction, chamfered to be round. The chamfered rounded corners 33a allow the protrusion 22 to easily mate with the slot-shaped recess 33 by guiding the protrusion 22 in the process of mating with the recess 33.

Furthermore, in this embodiment, as described above, the second light source 1b irradiates a fluorescent agent inside a subject body with near-infrared excitation light, and the near-infrared fluorescent sensor 6 detects near-infrared fluorescence, generated by radiation of the near-infrared excitation light from the second light source 1b and emitted from the inside of the subject body. With the above configuration, the near-infrared fluorescent imaging device 100 detecting near-infrared fluorescence emitted from the inside of a subject body is capable of having the operation unit 20 rested in a stable condition.

Modification

The described embodiment is an example only in every aspect and is not intended to be limiting. The scope of the present disclosure is presented not in the above embodiment but in the appended claims, and includes all changes (modifications) within the range of the appended claims and the equivalents.

More specifically, the above embodiment describes an example in which a protrusion of an operation unit and a recess on an upper surface of a device body are mated with each other; however, the present disclosure is not limited to this configuration. In another configuration, the operation unit and the upper surface of the device body may be mated with each other using shapes (configurations) other than a protrusion and a recess.

In the above embodiment, the operation unit has a protrusion, whereas the device body has a recess on its upper surface. The present disclosure is not limited to this exemplary configuration. For example, the operation unit may have a recess, whereas the device body may have a protrusion on its upper surface.

In the above embodiment, the protrusion of the operation unit and the recess on the upper surface of the device body are substantially linearly extended; however, the present disclosure is not limited to this exemplary configuration. For example, the protrusion of the operation unit and the recess on the upper surface of the device body may have shapes (such as an arc) other than a substantially straight line.

In the above embodiment, the protrusion is formed from an end to the other end in a direction along the short side of the substantially rectangular operation unit; however, the present disclosure is not limited to this exemplary configuration. The protrusion may be partially formed between the ends in a direction along the short side of the substantially rectangular operation unit.

In the above embodiment, the recess and the protrusion are both chamfered; however, the present disclosure is not limited to this exemplary configuration. Only the recess may be chamfered.

Figure 7:
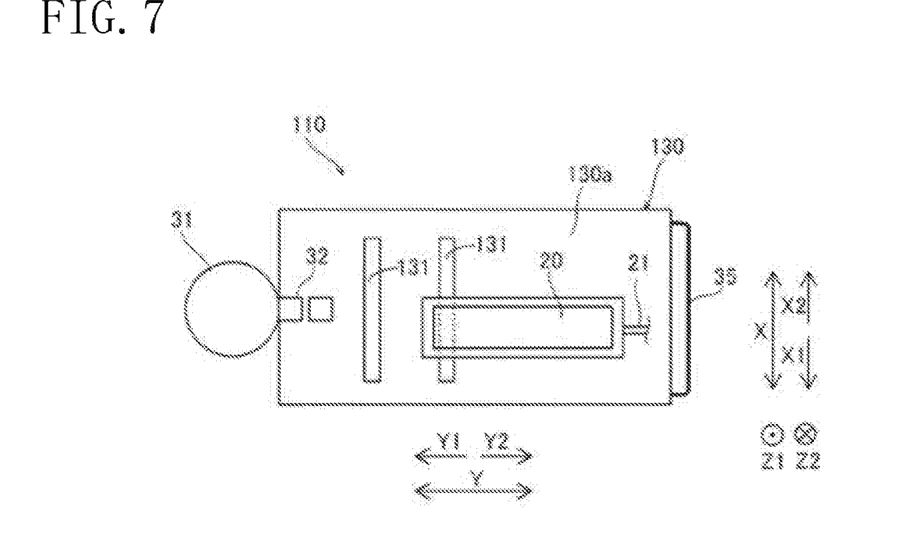
FIG. 7 is a top view of a near-infrared fluorescent imaging device according to a first modification of the embodiment of the present disclosure.

In the above embodiment, the device body has one recess on its upper surface; however, the present disclosure is not limited to this exemplary configuration. As a near-infrared fluorescent imaging device 110 of a first modification illustrated in FIG. 7, a device body 130 may have a plurality of recesses 131 (two recesses in the first modification) on an upper surface 130a of the device body 130. This configuration allows the operation unit 20 to be rested in a stable condition at a plurality of locations on the upper surface 130a of the device body 130. The recess 131 is an example of the "first mating portion" in the appended claims. The near-infrared fluorescent imaging device 110 is an example of the "medical imaging device" in the appended claims.

Figure 8:
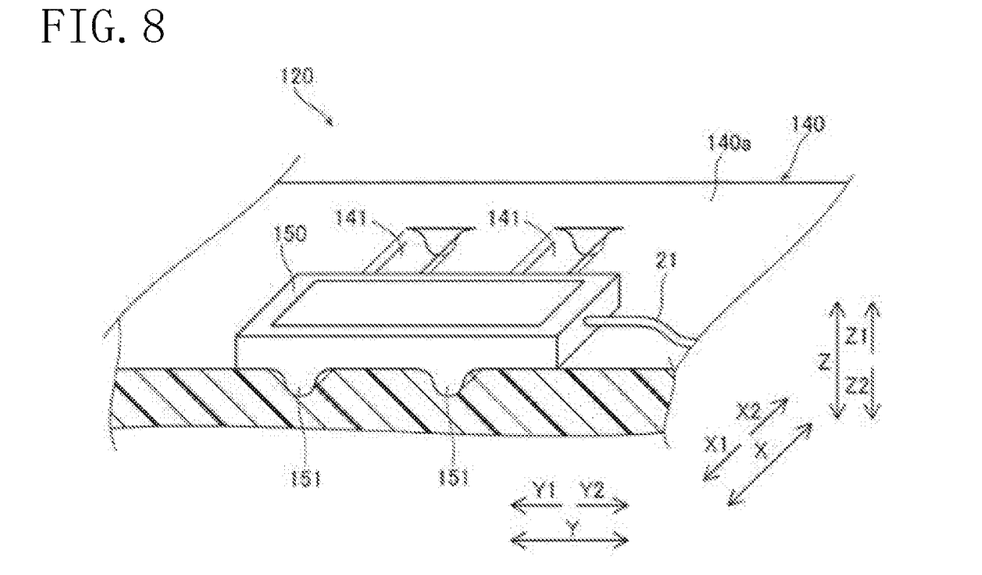
FIG. 8 is a perspective view of a near-infrared fluorescent imaging device according to a second modification of the embodiment of the present disclosure.

In the above embodiment, the operation unit has one protrusion; however, the present disclosure is not limited to this exemplary configuration. For example, as a near-infrared fluorescent imaging device 120 of a second modification illustrated in FIG. 8, a device body 140 may have a plurality (for example, two recesses) of recesses 141 on an upper surface 140a of the device body 140, and an operation unit 150 may have a plurality (for example, two protrusions) of protrusions 151 mating with the respective recesses 141. The recess 141 is an example of the "first mating portion" in the appended claims. The protrusion 151 is an example of the "second mating portion" in the appended claims. The near-infrared fluorescent imaging device 120 is an example of the "medical imaging device" in the appended claims.

In the above embodiments, the near-infrared fluorescent imaging device includes one operation unit; however, the present disclosure is not limited to this exemplary configuration. For example, the near-infrared fluorescent imaging device may include a plurality of operation units.

In the above embodiments, the present disclosure is applied to a near-infrared fluorescent imaging device; however, without being limited to this application, the present disclosure may be applied to any medical imaging device other than a near-infrared fluorescent imaging device.

What is claimed is:

1. A medical imaging device comprising:
a light source unit configured to irradiate a contrast agent inside a subject body with light;
a detection unit configured to detect light emitted from the inside of the subject body generated by radiation of the light from the light source unit with respect to the subject body;
a device body provided with the light source unit and the detection unit;
an operation unit configured to be movable and provided separately from the device body to operate the device, and
wherein an upper surface of the device body is provided with a first mating portion, and the operation unit has a second mating portion configured to movably mate with the first mating portion in a predetermined direction, and an operation portion formed on the operation unit is configured to be operable by a user at different positions in the predetermined direction along the upper surface of the device body by moving the operation unit with the second mating portion of the operation unit mating with the first mating portion,
wherein the first mating portion has a length larger than a width of the operation unit in the predetermined direction when the second mating portion of the operation unit mates with the first mating portion, and the second mating portion extends along a direction perpendicular to a direction in which the operation unit is pulled by a weight of a cable of the operation unit when the second mating portion of the operation unit mates with the first mating portion,
wherein the upper surface of the device body has the first mating portion and the operation unit has the second mating portion configured to movably mate with the first mating portion, the first mating portion being recessed and the second mating portion protruding,
wherein the second mating portion is formed to extend from an end to the other end of the operation unit in a width direction of the operation unit as the predetermined direction.

2. The medical imaging device of claim 1, wherein the recessed first mating portion is slot-shaped and is substantially linearly extended along the predetermined direction, and the protruding second mating portion is substantially linearly extended along the predetermined direction and is configured to be slidably movable along the slot-shaped first mating portion while mated with the slot-shaped first mating portion.

3. The medical imaging device of claim 2, wherein the device body is configured to be movable in a direction, and
the slot-shaped first mating portion is substantially linearly extended along a direction perpendicular to the direction in which the device body is capable of moving.

4. The medical imaging device of claim 2, wherein the operation unit is connected with the device body using the cable, and the slot-shaped first mating portion is substantially linearly extended along a direction perpendicular to the direction in which the operation unit is pulled by the weight of the cable.

5. The medical imaging device of claim 2, wherein a length of the slot-shaped first mating portion in a direction along the predetermined direction is larger than a length of the protruding second mating portion in a direction along the predetermined direction.

6. The medical imaging device of claim 2, wherein the device body includes a side surface perpendicular to the upper surface, and
the slot-shaped first mating portion has wall portions at a first end and a second end in a direction along the predetermined direction, for avoiding the first end and the second end of the slot-shaped first mating portion from reaching the side surface.

7. The medical imaging device of claim 2, wherein an opening end surface of the slot-shaped first mating portion is chamfered to be round.

8. The medical imaging device of claim 1, wherein the first mating portion includes a plurality of first mating portions formed on the upper surface of the device body.

9. The medical imaging device of claim 1, wherein the contrast agent capable of being used inside the subject body includes a fluorescent agent, the light source unit is configured to irradiate the fluorescent agent inside the subject body with near-infrared excitation light, and the detection unit is configured to detect near-infrared fluorescence generated by radiation of the near-infrared excitation light from the light source unit and emitted from the inside of the subject body.

10. A medical imaging device comprising:

a light source unit configured to irradiate a contrast agent inside a subject body with light;

a detection unit configured to detect light emitted from the inside of the subject body generated by radiation of the light from the light source unit with respect to the subject body;

a device body provided with the light source unit and the detection unit;

an operation unit configured to be movable and provided separately from the device body to operate the device, and wherein an upper surface of the device body is provided with a first mating portion, and the operation unit has a second mating portion configured to movably mate with the first mating portion in a predetermined direction, and an operation portion formed on the operation unit is configured to be operable by a user at different positions in the predetermined direction along the upper surface of the device body by moving the operation unit with the second mating portion of the operation unit mating with the first mating portion, wherein the first mating portion has a length larger than a width of the operation unit in the predetermined direction when the second mating portion of the operation unit mates with the first mating portion, wherein the upper surface of the device body has the first mating portion and the operation unit has the second mating portion configured to movably mate with the first mating portion, the first mating portion being recessed and the second mating portion protruding, wherein the second mating portion is formed to extend from an end to the other end of the operation unit in a width direction of the operation unit as the predetermined direction.

* * * * *